(12) United States Patent
Gubler

(10) Patent No.: US 11,484,547 B2
(45) Date of Patent: Nov. 1, 2022

(54) COMPOSITIONS AND METHODS FOR CHOLESTEROL, GLUCOSE AND MICROBIOME CONTROL

(71) Applicant: Performance Labs PTE. LTD., Singapore (SG)

(72) Inventor: Daniel Gubler, Orem, UT (US)

(73) Assignee: PERFORMANCE LABS PTE. LTD., Singapore (SG)

( * ) Notice: Subject to any disclaimer, the term of this patent is extended or adjusted under 35 U.S.C. 154(b) by 0 days.

(21) Appl. No.: 16/241,609

(22) Filed: Jan. 7, 2019

(65) Prior Publication Data

US 2019/0209600 A1 Jul. 11, 2019

Related U.S. Application Data

(60) Provisional application No. 62/614,670, filed on Jan. 8, 2018.

(51) Int. Cl.

| | | |
|---|---|---|
| A61K 31/714 | (2006.01) | |
| A61K 31/736 | (2006.01) | |
| A61K 31/733 | (2006.01) | |
| A61K 36/87 | (2006.01) | |
| A61K 36/73 | (2006.01) | |
| A61P 3/08 | (2006.01) | |
| A61P 9/00 | (2006.01) | |
| A23L 29/238 | (2016.01) | |
| A61K 31/07 | (2006.01) | |
| A61K 31/355 | (2006.01) | |
| A61K 31/315 | (2006.01) | |
| A61K 31/525 | (2006.01) | |
| A61K 31/455 | (2006.01) | |
| A61K 31/51 | (2006.01) | |
| A61K 31/4188 | (2006.01) | |
| A61K 31/59 | (2006.01) | |
| A61K 31/375 | (2006.01) | |
| A23L 33/21 | (2016.01) | |
| A23L 33/00 | (2016.01) | |
| A23L 33/15 | (2016.01) | |
| A61K 36/064 | (2006.01) | |
| A61K 31/732 | (2006.01) | |
| A61K 31/715 | (2006.01) | |
| A61K 36/61 | (2006.01) | |

(52) U.S. Cl.
CPC .......... *A61K 31/714* (2013.01); *A23L 29/238* (2016.08); *A23L 33/15* (2016.08); *A23L 33/21* (2016.08); *A23L 33/30* (2016.08); *A61K 31/07* (2013.01); *A61K 31/315* (2013.01); *A61K 31/355* (2013.01); *A61K 31/375* (2013.01); *A61K 31/4188* (2013.01); *A61K 31/455* (2013.01); *A61K 31/51* (2013.01); *A61K 31/525* (2013.01); *A61K 31/59* (2013.01); *A61K 31/715* (2013.01); *A61K 31/732* (2013.01); *A61K 31/733* (2013.01); *A61K 31/736* (2013.01); *A61K 36/064* (2013.01); *A61K 36/61* (2013.01); *A61K 36/73* (2013.01); *A61K 36/87* (2013.01); *A61P 3/08* (2018.01); *A61P 9/00* (2018.01)

(58) Field of Classification Search
None
See application file for complete search history.

(56) References Cited

U.S. PATENT DOCUMENTS

| | | | |
|---|---|---|---|
| 4,824,672 A | 4/1989 | Day et al. | |
| 4,883,788 A | 11/1989 | Day et al. | |
| 5,422,101 A | 6/1995 | Daggy et al. | |
| 7,030,092 B1 * | 4/2006 | Levine | A23L 29/238 426/590 |
| 7,767,245 B2 * | 8/2010 | Grossman | A23L 33/105 426/548 |
| 8,361,517 B2 * | 1/2013 | Bourgeois-Lugand | A61K 31/07 424/725 |
| 2008/0268024 A1 * | 10/2008 | Rull Prous | A61K 36/77 424/439 |
| 2011/0027412 A1 * | 2/2011 | Spence | A23L 33/22 426/560 |
| 2011/0142990 A1 | 6/2011 | Jacob | |
| 2013/0261183 A1 | 10/2013 | Bhagat | |
| 2014/0308389 A1 | 10/2014 | Ames et al. | |

FOREIGN PATENT DOCUMENTS

EP 1859690 A1 11/2007

OTHER PUBLICATIONS

Ryan et al., "Oat-based breakfast cereals are a rich source of polyphenols and high in antioxidant potential" Journal of Food Composition and Analysis vol. 24 pp. 929-934 (Year: 2011).*

Fava et al., "The Gut Microbiota and Lipid Metabolism: Implications for Human Health and Coronary Heart Disease" Current Medicinal Chemistry vol. 13 pp. 3005-3021 (Year: 2006).*

Miremadi et al., "Health promoting effect of synbiotic yogurt containing pomegranate polyphenols: Scientific evidence" EMAS2017/Maturitas vol. 100 p. 141 abstract O32 (Year: 2017).*

Aprikian et al., "Apple Pectin and a Polyphenol-Rich Apple Concentrate Are More Effective Together Than Separately on Cecal Fermentations and Plasma Lipids in Rats" Journal of Nutrition vol. 133 No. 6 pp. 1860-1865 (Year: 2003).*

(Continued)

*Primary Examiner* — Eric Olson
(74) *Attorney, Agent, or Firm* — Edwin S. Flores; Daniel J. Chalker; Chalker Flores, LLP

(57) ABSTRACT

The present invention includes compositions and methods for reducing at least one of fasting blood glucose, total cholesterol, LDL cholesterol, VLDL cholesterol, a cholesterol:HDL ratio, triglycerides, or increasing a healthy microbiome comprising a synergistic amount of a fiber blend, a polyphenol blend, and a multivitamin supplement in an amount sufficient to lower at fasting blood glucose, total cholesterol, LDL cholesterol, VLDL cholesterol, a cholesterol:HDL ratio, triglycerides, or increasing a healthy microbiome.

15 Claims, No Drawings

(56) References Cited

OTHER PUBLICATIONS

Martin-Carron et al., "Reduction in Serum Total and LDL Cholesterol Concentrations by a Dietary Fiber and Polyphenol-Rich Grape Product in Hypercholesterolemic Rats" Nutrition Research vol. 19 No. 9 pp. 1371-1378 (Year: 1999).*
Sharma et al., "Hypocholesterolemic effect of gum acacia in men" Nutrition Research vol. 5, Issue 12, Dec. 1985, pp. 1321-1326 (Year: 1985).*
Brouns et al., "Cholesterol-lowering properties of different pectin types in mildly hyper-cholesterolemic men and women" European Journal of Clinical Nutrition vol. 66 pp. 591-599 (Year: 2012).*
Jurgonski et al., "Does dietary Inulin affect the biological properties of grapefruit flavonoids in rats?" Ann Nutr Metab vol. 58 suppl 3 p. 3 abstracr 27/335 (Year: 2011).*
Bondonno et al., "The cardiovascular benefits of apples: Whole fruit vs. isolated compounds" Trends in Food Science and Technology vol. 69 pp. 423-256 (Year: 2017).*
Moreno-Indias et al., "Red wine polyphenols modulate fecal microbiota and reduce markers of the metabolic syndrome in obese patients" Food and Function vol. 7 pp. 1775-1787 (Year: 2016).*
Reveneau et al., "Phenylacetic and Phenylpropionic Acids Do Not Affect Xylan Degradation by Ruminococcus albus" Applied and Environmental Microbiology vol. 69 No. 11 pp. 6954-6958 (Year: 2003).*
Verhoog et al., "Dietary Factors and Modulation of Bacteria Strains of Akkermansia muciniphila and Faecalibacterium prausnitzii: A Systematic Review" Nutrients vol. 11 p. 1565 (Year: 2019).*
United States Patent & Trademark Office, International Search Report and Written Opinion of the International Searching Authority for PCT/US2019/012636 dated Apr. 3, 2019, 3 pp.

* cited by examiner

COMPOSITIONS AND METHODS FOR CHOLESTEROL, GLUCOSE AND MICROBIOME CONTROL

CROSS-REFERENCE TO RELATED APPLICATIONS

This patent application claims priority to U.S. provisional patent application Ser. No. 62/614,670 filed on Jan. 8, 2018 entitled "Compositions and Methods for Cholesterol, Glucose, and Microbiome Control," all of which is hereby incorporated by reference in its entirety.

STATEMENT OF FEDERALLY FUNDED RESEARCH

Not applicable.

TECHNICAL FIELD OF THE INVENTION

The present invention relates in general to the field of novel compositions and methods that synergistically control cholesterol, glucose, and provide for an improved, healthy microbiome.

BACKGROUND OF THE INVENTION

Without limiting the scope of the invention, its background is described in connection with dietary supplementation to reduce bad cholesterol, reduce fasting glucose levels, and/or improve the diversity of the microbiome.

One such patent is U.S. Pat. No. 7,030,092, issued to Levine, entitled "Ultra-high fiber supplement and method of reducing weight cardiovascular risks and ingested toxins." Briefly, this inventor is said to teach an improved ultra-high fiber supplement that promotes satiety, caloric reduction, and weight loss. The supplement is said to comprise: guar, oat, psyllium, locust bean gum, pectin, green tea, multianthocyanadins, pyridoxine, and folic acid. The supplement is further said to improve cardiovascular health and reduces cardiovascular inflammation and the risk of heart disease. The composition may also include antioxidants, including green tea, improves weight loss, and general and cardiovascular health, including: reducing serum lipoprotein oxidation and risk of free-radical related diseases, lowering of plasma homocysteine by the addition of folic acid and pyridoxine.

Another such patent is U.S. Pat. No. 5,422,101, issued to Daggy, et al., entitled, "Cholesterol lowering drink mix compositions." These inventors are said to teach a psyllium husk-containing drink mix compositions comprising psyllium husk, an anion exchange resin, and edible, water soluble salts. The edible, water-soluble salts are said to be present at a level sufficient to reduce the gellation rate of the psyllium husk and anion exchange resin-containing composition when dispersed in an aqueous solution.

Another such patent is U.S. Pat. No. 4,883,788, issued to Day, et al., entitled, "Method and composition for reducing serum cholesterol". These inventors teach an orally administrable composition and method for reducing serum cholesterol levels that comprises guar gum, and a dispersing mineral salt such as, for example, calcium carbonate, magnesium carbonate, or potassium carbonate, is administered to humans to reduce serum cholesterol levels. More particularly, these inventors claimed an orally-administrable pharmaceutical composition for use in reducing serum cholesterol levels consisting essentially of: (a) an effective amount of guar gum which exhibits cholesterol-reducing activity, and (b) a dispersibility-enhancing amount of an orally-ingestible non-toxic pharmacologically-acceptable mineral salt capable of dissolution in the gastric fluid with release of a gas, the ratio of guar gum to said mineral salt being in the range of approximately 3:1 to approximately 10:1.

Another such patent is U.S. Pat. No. 4,824,672, also issued to Day, et al., entitled "Method and composition for reducing serum cholesterol", which is directed to an orally administrable composition and method for reducing serum cholesterol levels comprising a gel-forming fiber such as, for example, guar gum, psyllium seed, pectin, glucomannan, oat and barley and a mineral salt such as for example, calcium carbonate, magnesium carbonate and potassium carbonate is administered to humans to reduce serum cholesterol levels. More particularly, these inventors claimed an orally administrable pharmaceutical composition for use in reducing serum cholesterol levels consisting essentially of: (a) an effective amount of a gel-forming fiber which exhibits cholesterol reducing activity, and (b) an orally ingestible non-toxic mineral salt capable of dissolution in the gastric fluid with release of carbon dioxide.

However, despite these advances, a need remains for an improved composition that provides for improved fasting blood glucose, cholesterol levels, and other increases in patient health.

SUMMARY OF THE INVENTION

In one embodiment, the present invention includes a composition for reducing at least one of fasting blood glucose, total cholesterol, LDL cholesterol, VLDL cholesterol, cholesterol:HDL ratio, triglycerides, or increasing a healthy microbiome comprising a synergistic amount of a fiber blend, a polyphenol blend, and a multivitamin supplement in an amount sufficient to lower at fasting blood glucose, total cholesterol, LDL cholesterol, VLDL cholesterol, cholesterol:HDL ratio, triglycerides, or increasing the healthy microbiome. In one aspect, the fiber blend comprises fructooligosaccharides and one or more polysaccharides selected from, guar gum, gum Arabic, locust bean gum, citrus pectin, or oat fiber. In another aspect, the polyphenol blend comprises two or more polyphenols selected from yeast, apple extract, pomegranate extract, or red grape extract. In another aspect, the increase in the healthy microbiome comprises an increase in one or more bacteria selected from *Lactobacillus, Roseburia, Prevotella, Ruminococcus albus, Akkermansia muciniphila, Bifidobacterium, Oxalobacter formingenes, Odoribacter*, or *Anaerotruncus colihominis*. In another aspect, the multivitamin supplement is selected from Vitamin A, Vitamin C, Vitamin E, Thiamin, Riboflavin, Niacin, Vitamin B6, Folic acid, Vitamin B12, Biotin, Calcium, and Zinc. In another aspect, the fiber blend comprises fructooligosaccharides, guar gum, gum Arabic, locust bean gum, citrus pectin, and oat fiber. In another aspect, the polyphenol blend comprises yeast, apple extract, pomegranate extract, and red grape extract. In another aspect, the composition further comprises one or more excipients, flavorants, sweeteners, or organoleptic agents. In another aspect, the composition has a synergistic effect on the fasting blood glucose, total cholesterol, LDL cholesterol, VLDL cholesterol, cholesterol:HDL ratio, triglycerides, or improving the healthy microbiome when compared to a composition without at least one of: fructooligosaccharides, yeast, apple extract, pomegranate extract, or red grape extract. In another aspect, the composition is provided in an amount that increases microbiome diversity to reduce the symptoms of Irritable Bowel Syndrome, diarrhea, obesity, Type II Diabetes, Crohn's Disease, ulcerative colitis, kidney stones, Inflammatory Bowel Disease, or constipation. In another aspect, the composition lowers at fasting blood glucose, total cholesterol, LDL cholesterol, VLDL cholesterol, cholesterol:HDL ratio, or triglycerides. In another aspect, the composition consists essentially of a fiber blend, a polyphenol blend, a multivitamin supplement, and one or more inactive excipients. In another aspect, the fiber blend consists essentially of fructooligosaccharides and one or more polysaccharides selected from, guar gum, gum Arabic, locust bean gum, citrus pectin, and oat fiber. In another aspect, the polyphenol blend consists essentially of yeast, apple extract, pomegranate extract, and red grape extract. In another aspect, the composition consists of a fiber blend, a polyphenol blend, and a multivitamin supplement.

In another embodiment, the present invention includes a method for reducing at least one of fasting blood glucose, total cholesterol, LDL cholesterol, VLDL cholesterol, a cholesterol:HDL ratio, triglycerides, or increasing a healthy microbiome in a human subject comprising: identifying a subject in need for reduced fasting blood glucose, total cholesterol, LDL cholesterol, VLDL cholesterol, a cholesterol:HDL ratio, triglycerides, or increased healthy microbiome; and providing the subject with a synergistic amount of a fiber blend, a polyphenol blend, and a multivitamin supplement in an amount sufficient to lower at fasting blood glucose, total cholesterol, LDL cholesterol, VLDL cholesterol, cholesterol:HDL ratio, triglycerides, or increasing the healthy microbiome. In one aspect, the fiber blend comprises fructooligosaccharides and one or more polysaccharides selected from, guar gum, gum Arabic, locust bean gum, citrus pectin, or oat fiber. In another aspect, the polyphenol blend comprises two or more polyphenols selected from yeast, apple extract, pomegranate extract, or red grape extract. In another aspect, the increase in the healthy microbiome comprises an increase in one or more bacteria selected from *Lactobacillus, Roseburia, Prevotella, Ruminococcus albus, Akkermansia muciniphila, Bifidobacterium, Oxalobacter formingenes, Odoribacter,* or *Anaerotruncus colihominis*. In another aspect, the composition is provided in an amount that increases microbiome diversity to reduce the symptoms of Irritable Bowel Syndrome, diarrhea, obesity, Type II Diabetes, Crohn's Disease, ulcerative colitis, kidney stones, Inflammatory Bowel Disease, or constipation. In another aspect, the multivitamin supplement is selected from Vitamin A, Vitamin C, Vitamin E, Thiamin, Riboflavin, Niacin, Vitamin B6, Folic acid, Vitamin B12, Biotin, Calcium, and Zinc. In another aspect, the fiber blend comprises fructooligosaccharides, guar gum, gum Arabic, locust bean gum, citrus pectin, and oat fiber. In another aspect, the polyphenol blend comprises yeast, apple extract, pomegranate extract, and red grape extract. In another aspect, the method further comprises one or more excipients, flavorants, sweeteners, or organoleptic agents. In another aspect, the method further comprises the step of determining a microbiome of the subject prior to use of the composition and after a predetermined period of time measuring the microbiome to detect changes in the microbiome. In another aspect, the composition has a synergistic effect on the fasting blood glucose, total cholesterol, LDL cholesterol, VLDL cholesterol, cholesterol:HDL ratio, triglycerides, or improving the healthy microbiome when compared to a composition without at least one of: fructooligosaccharides, yeast, apple extract, pomegranate extract, or red grape extract. In another aspect, the composition consists essentially of a fiber blend, a polyphenol blend, a multivitamin supplement, and one or more inactive excipients. In another aspect, the fiber blend consists essentially of fructooligosaccharides and one or more polysaccharides selected from, guar gum, gum Arabic, locust bean gum, citrus pectin, and oat fiber. In another aspect, the polyphenol blend consists essentially of yeast, apple extract, pomegranate extract, and red grape extract. In another aspect, the composition consists of a fiber blend, a polyphenol blend, and a multivitamin supplement.

In another embodiment, the present invention includes a method of changing a gastrointestinal microbiome to reduce fasting blood glucose, total cholesterol, LDL cholesterol, VLDL cholesterol, cholesterol:HDL ratio, triglycerides of a human subject comprising: administering to the subject a pharmaceutical composition comprising a glycan therapeutic preparation in an amount effective to treat dysbiosis of the gastrointestinal microbiota, comprising a synergistic amount of a fiber blend, a polyphenol blend, and a multivitamin supplement in an amount sufficient to change the microbiome to reduce fasting blood glucose, total cholesterol, LDL cholesterol, VLDL cholesterol, cholesterol:HDL ratio, triglycerides. In one aspect, the fiber blend comprises fructooligosaccharides and one or more polysaccharides selected from, guar gum, gum Arabic, locust bean gum, citrus pectin, or oat fiber. In another aspect, the polyphenol blend comprises two or more polyphenols selected from yeast, apple extract, pomegranate extract, or red grape extract. In another aspect, the increase a healthy microbiome that comprises an increase in one or more bacteria selected from *Lactobacillus, Roseburia, Prevotella, Ruminococcus albus, Akkermansia muciniphila, Bifidobacterium, Oxalobacter formingenes, Odoribacter,* or *Anaerotruncus colihominis*. In another aspect, the composition is provided in an amount that increases microbiome diversity to reduce the symptoms of Irritable Bowel Syndrome, diarrhea, obesity, Type II Diabetes, Crohn's Disease, ulcerative colitis, kidney stones, Inflammatory Bowel Disease, or constipation. In another aspect, the multivitamin supplement is selected from Vitamin A, Vitamin C, Vitamin E, Thiamin, Riboflavin, Niacin, Vitamin B6, Folic acid, Vitamin B12, Biotin, Calcium, and Zinc. In another aspect, the fiber blend comprises fructooligosaccharides, guar gum, gum Arabic, locust bean gum, citrus pectin, and oat fiber. In another aspect, the polyphenol blend comprises yeast, apple extract, pomegranate extract, and red grape extract. In another aspect, the method further comprises one or more excipients, flavorants, sweeteners, or organoleptic agents. In another aspect, the method further comprises the step of determining a microbiome of the subject prior to use of the composition and after a predetermined period of time measuring the microbiome to detect changes in the microbiome. In another aspect, the composition has a synergistic effect on the fasting blood glucose, total cholesterol, LDL cholesterol, VLDL cholesterol, cholesterol:HDL ratio, triglycerides when compared to a composition without at least one of: fructooligosaccharides, yeast, apple extract, pomegranate extract, or red grape extract. In another aspect, the composition consists essentially of a fiber blend, a polyphenol blend, a multivitamin supplement, and one or more inactive excipients. In another aspect, the fiber blend consists essentially of fructooligosaccharides and one or more polysaccharides selected from, guar gum, gum Arabic, locust bean gum, citrus pectin, and oat fiber. In another aspect, the polyphenol blend consists essentially of yeast, apple extract, pomegranate extract, and red grape extract. In another aspect, the composition consists of a fiber blend, a polyphenol blend, and a multivitamin supplement.

DETAILED DESCRIPTION OF THE INVENTION

While the making and using of various embodiments of the present invention are discussed in detail below, it should be appreciated that the present invention provides many applicable inventive concepts that can be embodied in a wide variety of specific contexts. The specific embodiments discussed herein are merely illustrative of specific ways to make and use the invention and do not delimit the scope of the invention.

To facilitate the understanding of this invention, a number of terms are defined below. Terms defined herein have meanings as commonly understood by a person of ordinary skill in the areas relevant to the present invention. Terms such as "a", "an" and "the" are not intended to refer to only a singular entity, but include the general class of which a specific example may be used for illustration. The terminology herein is used to describe specific embodiments of the invention, but their usage does not limit the invention, except as outlined in the claims.

The present invention (hereinafter also referred to as Bios 7), is an improvement and upgrade from prior compositions such as Balance Glucose that are included in Bios Life C and Bios Life 2. Like Balance Glucose, Bios 7 provides satiety (fullness) and helps control blood glucose levels. Bios 7 includes the dietary fiber with additional ingredients to provide other health benefits. Surprisingly, the added compounds showed a synergistic effect when compared to the prior comparison composition. The present invention was able to suppress appetite, have a significant prebiotic effect by promoting healthy bacterial growth, an enhanced biodiversity in the microbiome, a strengthened immune response, and help ensure long-term gut health and overall health.

A direct comparative study was conducted to compare the present invention (referred to herein as Bios 7) with prior iterations of compositions (Bios Life C and Bios Life 2) and the measure the effect of the present invention on blood lipid levels, glucose control, and microbiome management.

Bios 7. Fiber blend comprises fructooligosaccharides and one, two, three, four, or five polysaccharides selected from, guar gum, gum Arabic, locust bean gum, citrus pectin, and/or oat fiber. Polyphenol blend comprises two, three, or four polyphenols selected from yeast, apple extract, pomegranate extract, and/or red grape extract. Multivitamin is selected Vitamin A, Vitamin C, Vitamin E, Thiamin, Riboflavin, Niacin, Vitamin B6, Folic acid, Vitamin B12, Biotin, Calcium, and/or Zinc. Other optional ingredients: maltodextrin, natural and artificial flavors, citric acid, juice powder, sweetener, and/or xantham gum.

Bios Life C. Guar gum, phytosterols (beta-sitosterol, campestrol, stigmasterol), gum Arabic, locust bean gum, pectin, oat fiber, natural orange flavor, calcium carbonate, ascorbic acid, Vitamin A, beta-carotene, beta glucan, sucralose, niacinamide, d-alpha tocophenyl acetate, chrysanthemum morifolium extract, cyanobalamin, policosanol, zinc gluconate, pyridoxine, riboflavin, folic acid, biotin, thiamine, and chromium.

Bios Life 2. Guar gum, gum Arabic, locust bean gum, pectin, oat fiber, natural orange flavor, calcium carbonate, ascorbic acid, Vitamin A, beta glucan, Stevia, beta-carotene, niacinamide, d-alpha tocophenyl acetate, maltodextrin, zinc gluconate, pyridoxine, riboflavin, biotin, thiamine, cyanobalamin, chromium, selenium, and folic acid.

Dosage Forms.

A dosage unit for use of the composition of the present invention, may be mixed together, form ionic or even covalent bonds. The fiber blend, a polyphenol blend, and/or a multivitamin supplement of the present invention may be administered in oral, intravenous (bolus or infusion), intraperitoneal, subcutaneous, or intramuscular form, all using dosage forms well known to those of ordinary skill in the pharmaceutical arts. Depending on the particular location or method of delivery, different dosage forms, e.g., tablets, capsules, pills, powders, granules, elixirs, tinctures, suspensions, syrups, and emulsions may be used to provide the fiber blend, polyphenol blend, and/or multivitamin supplement of the present invention to a patient in need of therapy. The fiber blend, polyphenol blend, and multivitamin supplement may also be administered as any one of the known salt forms of the fiber blend, polyphenol blend, and multivitamin supplement components.

A fiber blend, a polyphenol blend, and/or a multivitamin supplement can be administered in admixture with suitable pharmaceutical salts, buffers, diluents, extenders, excipients and/or carriers (collectively referred to herein as a pharmaceutically acceptable carrier or carrier materials) selected based on the intended form of administration and as consistent with conventional pharmaceutical practices. Depending on the best location for administration, the fiber blend, polyphenol blend, and/or multivitamin supplement may be formulated to provide, e.g., maximum and/or consistent dosing for the particular form for oral, rectal, topical, intravenous injection or parenteral administration. While the fiber blend, polyphenol blend, and/or multivitamin supplement may be administered alone, it will generally be provided in a stable salt form mixed with a pharmaceutically acceptable carrier. The carrier may be solid or liquid, depending on the type and/or location of administration selected.

Techniques and compositions for making useful dosage forms using the present invention are described in one or more of the following references: Anderson, Philip O.; Knoben, James E.; Troutman, William G, eds., Handbook of Clinical Drug Data, Tenth Edition, McGraw-Hill, 2002; Pratt and Taylor, eds., Principles of Drug Action, Third Edition, Churchill Livingston, N.Y., 1990; Katzung., ed., Basic and Clinical Pharmacology, Ninth Edition, McGraw Hill, 2007; Goodman and Gilman, eds., The Pharmacological Basis of Therapeutics, Tenth Edition, McGraw Hill, 2001; Remington's Pharmaceutical Sciences, 20th Ed., Lippincott Williams & Wilkins., 2000; Martindale, The Extra Pharmacopoeia, Thirty-Second Edition (The Pharmaceutical Press, London, 1999); all of which are incorporated by reference, and the like, relevant portions incorporated herein by reference.

For example, the fiber blend, polyphenol blend, and/or multivitamin supplement may be included in a tablet. Tablets may contain, e.g., suitable binders, lubricants, disintegrating agents, coloring agents, flavoring agents, flow-inducing agents and/or melting agents. For example, oral administration may be in a dosage unit form of a tablet, gelcap, caplet or capsule, the active drug component being combined with a non-toxic, pharmaceutically acceptable, inert carrier such as lactose, gelatin, agar, starch, sucrose, glucose, methyl cellulose, magnesium stearate, dicalcium phosphate, calcium sulfate, mannitol, sorbitol, mixtures thereof, and the like. Suitable binders for use with the present invention include: starch, gelatin, natural sugars (e.g., glucose or beta-lactose), corn sweeteners, natural and synthetic gums (e.g., acacia, tragacanth or sodium alginate), carboxymethylcellulose, polyethylene glycol, waxes, and the like. Lubricants for use with the invention may include: sodium oleate, sodium stearate, magnesium stearate, sodium benzoate, sodium acetate, sodium chloride, mixtures thereof, and the like. Disintegrators may include: starch, methylcellulose, agar, bentonite, xanthan gum, mixtures thereof, and the like.

The fiber blend, polyphenol blend, and/or multivitamin supplement may be administered in the form of liposome delivery systems, e.g., small unilamellar vesicles, large unilamellar vesicles, and multilamellar vesicles, whether charged or uncharged. Liposomes may include one or more: phospholipids (e.g., cholesterol), stearylamine and/or phosphatidylcholines, mixtures thereof, and the like.

The fiber blend, polyphenol blend, and/or multivitamin supplement may also be coupled to one or more soluble, biodegradable, bioacceptable polymers as drug carriers or as a prodrug. Such polymers may include: polyvinylpyrrolidone, pyran copolymer, polyhydroxylpropylmethacrylamide-phenol, polyhydroxyethylasparta-midephenol, or polyethyleneoxide-polylysine substituted with palmitoyl residues, mixtures thereof, and the like. Furthermore, the fiber blend, polyphenol blend, and/or multivitamin supplement may be coupled one or more biodegradable polymers to achieve controlled release of the fiber blend, a polyphenol blend, and a multivitamin supplement, biodegradable polymers for use with the present invention include: polylactic acid, polyglycolic acid, copolymers of polylactic and polyglycolic acid, polyepsilon caprolactone, polyhydroxy butyric acid, polyorthoesters, polyacetals, polydihydropyrans, polycyanoacylates, and crosslinked or amphipathic block copolymers of hydrogels, mixtures thereof, and the like.

In one embodiment, gelatin capsules (gelcaps) may include the fiber blend, polyphenol blend, and/or multivitamin supplement and powdered carriers, such as lactose, starch, cellulose derivatives, magnesium stearate, stearic acid, and the like. Like diluents may be used to make compressed tablets. Both tablets and capsules may be manufactured as immediate-release, mixed-release or sustained-release formulations to provide for a range of release of medication over a period of minutes to hours. Compressed tablets may be sugar coated or film coated to mask any unpleasant taste and protect the tablet from the atmosphere. An enteric coating may be used to provide selective disintegration in, e.g., the gastrointestinal tract.

For oral administration in a liquid dosage form, the oral fiber blend, polyphenol blend, and/or multivitamin supplement components may be combined with any oral, non-toxic, pharmaceutically acceptable inert carrier such as ethanol, glycerol, water, and the like. Examples of suitable liquid dosage forms include solutions or suspensions in water, pharmaceutically acceptable fats and oils, alcohols or other organic solvents, including esters, emulsions, syrups or elixirs, suspensions, solutions and/or suspensions reconstituted from non-effervescent granules and effervescent preparations reconstituted from effervescent granules. Such liquid dosage forms may contain, for example, suitable solvents, preservatives, emulsifying agents, suspending agents, diluents, sweeteners, thickeners, and melting agents, mixtures thereof, and the like.

Liquid dosage forms of the fiber blend, polyphenol blend, and/or multivitamin supplement for oral administration may also include coloring and flavoring agents that increase patient acceptance and therefore compliance with a dosing regimen. In general, water, a suitable oil, saline, aqueous dextrose (e.g., glucose, lactose and related sugar solutions) and glycols (e.g., propylene glycol or polyethylene glycols) may be used as suitable carriers for parenteral solutions. Solutions for parenteral administration include generally, a water soluble salt of the active ingredient, suitable stabilizing agents, and if necessary, buffering salts. Antioxidizing agents such as sodium bisulfite, sodium sulfite and/or ascorbic acid, either alone or in combination, are suitable stabilizing agents. Citric acid and its salts and sodium EDTA may also be included to increase stability. In addition, parenteral solutions may include pharmaceutically acceptable preservatives, e.g., benzalkonium chloride, methyl- or propyl-paraben, and/or chlorobutanol. Suitable pharmaceutical carriers are described in Remington's Pharmaceutical Sciences, Mack Publishing Company, a standard reference text in this field, relevant portions incorporated herein by reference.

Capsules. Capsules may be prepared by filling standard two-piece hard gelatin capsules each with the fiber blend, polyphenol blend, and/or multivitamin supplement, 10 to 500 milligrams of powdered active ingredient, 5 to 150 milligrams of lactose, 5 to 50 milligrams of cellulose and 6 milligrams magnesium stearate.

Soft Gelatin Capsules. A mixture of active ingredients (the fiber blend, polyphenol blend, and/or multivitamin supplement) is dissolved in a digestible oil such as soybean oil, cottonseed oil or olive oil. The active ingredient is prepared and injected by using a positive displacement pump into gelatin to form soft gelatin capsules containing, e.g., 100-500 milligrams of the active ingredient. The capsules are washed and dried.

Tablets. A large number of tablets are prepared by conventional procedures so that the dosage unit was 100-1,500 milligrams of the fiber blend, polyphenol blend, and/or multivitamin supplement, 0.2 milligrams of colloidal silicon dioxide, 5 milligrams of magnesium stearate, 50-275 milligrams of microcrystalline cellulose, 11 milligrams of starch and 98.8 milligrams of lactose. Appropriate coatings may be applied to increase palatability or delay absorption.

To provide an effervescent tablet with the fiber blend, polyphenol blend, and/or multivitamin supplement, appropriate amounts of, e.g., monosodium citrate and sodium bicarbonate, are blended together and then roller compacted, in the absence of water, to form flakes that are then crushed to give granulates. The granulates are then combined with the active ingredient, drug and/or salt thereof, conventional beading or filling agents and, optionally, sweeteners, flavors and lubricants.

Suspension. An aqueous suspension is prepared for oral administration so that each 5 ml contain 100 mg of finely divided active ingredients (fiber blend, polyphenol blend, and/or multivitamin supplement), 200 mg of sodium carboxymethyl cellulose, 5 mg of sodium benzoate, 1.0 g of sorbitol solution, U.S.P., and 0.025 ml of vanillin.

For mini-tablets, the fiber blend, polyphenol blend, and/or multivitamin supplement are compressed into a hardness in the range 6 to 12 Kp. The hardness of the final tablets is influenced by the linear roller compaction strength used in preparing the granules or granulates, which are influenced by the particle size of, e.g., the monosodium hydrogen carbonate and sodium hydrogen carbonate. For smaller particle sizes, a linear roller compaction strength of about 15 to 20 KN/cm may be used.

Examples of suitable oral dosage forms include solutions or suspensions in water, pharmaceutically acceptable fats and oils, alcohols or other organic solvents, including esters, emulsions, syrups or elixirs, suspensions, solutions and/or suspensions reconstituted from non-effervescent granules and effervescent preparations reconstituted from effervescent granules. Such liquid dosage forms may contain, for example, suitable solvents, preservatives, emulsifying agents, suspending agents, diluents, sweeteners, thickeners, and melting agents. Oral dosage forms optionally contain flavorants and coloring agents. Parenteral and intravenous forms may also include minerals and other materials to make them compatible with the type of injection or delivery system chosen.

The composition of the fiber blend, polyphenol blend, and/or multivitamin supplement may be formulated for release that is immediate, rapid, extended, bi-phasic, etc. By "immediate release" is meant a release of an active agent to an environment over a period of seconds to no more than about 30 minutes once release has begun and release begins within no more than about 2 minutes after administration. An immediate release does not exhibit a significant delay in the release of drug. By "rapid release" is meant a release of an active agent to an environment over a period of 1-59 minutes or 0.1 minute to three hours once release has begun and release can begin within a few minutes after administration or after expiration of a delay period (lag time) after administration. As used herein, the term "extended release" profile assumes the definition as widely recognized in the art of pharmaceutical sciences. An extended release dosage form will release drug at substantially constant rate over an extended period of time or a substantially constant amount of drug will be released incrementally over an extended period of time. An extended release tablet generally effects at least a two-fold reduction in dosing frequency as compared to the drug presented in a conventional dosage form (e.g., a solution or rapid releasing conventional solid dosage forms). By "controlled release" is meant a release of an active agent to an environment over a period of about eight hours up to about 12 hours, 16 hours, 18 hours, 20 hours, a day, or more than a day. By "sustained release" is meant an extended release of an active agent to maintain a constant drug level in the blood or target tissue of a subject to which the device is administered. The term "controlled release", as regards to drug release, includes the terms "extended release", "prolonged release", "sustained release", or "slow release", as these terms are used in the pharmaceutical sciences. An controlled release can begin within a few minutes after administration or after expiration of a delay period (lag time) after administration.

A slow release dosage form is one that provides a slow rate of release of drug so that drug is released slowly and approximately continuously over a period of 3 hours, 6 hours, 12 hours, 18 hours, a day, 2 or more days, a week, or 2 or more weeks, for example.

A timed-release dosage form is one that begins to release drug after a predetermined period of time as measured from the moment of initial exposure to the environment of use.

A targeted release dosage form generally refers to an oral dosage form that designed to deliver the fiber blend, polyphenol blend, and/or multivitamin supplement to a particular portion of the gastrointestinal tract of a subject. An exemplary targeted dosage form is an enteric dosage form that delivers a drug into the middle to lower intestinal tract but not into the stomach or mouth of the subject. Other targeted dosage forms can deliver to other sections of the gastrointestinal tract such as the stomach, jejunum, ileum, duodenum, cecum, large intestine, small intestine, colon, or rectum.

By "delayed release" it is meant that initial release of the fiber blend, the polyphenol blend, and/or the multivitamin supplement occurs after expiration of an approximate delay (or lag) period. For example, if release of drug from an extended release composition is delayed two hours, then release of drug from begins at about two hours after administration of the composition, or dosage form, to a subject. In general, a delayed release is opposite an immediate release, wherein release of drug begins after no more than a few minutes after administration. Accordingly, the drug release profile from a particular composition can be a delayed-extended release or a delayed-rapid release. A "delayed-extended" release profile is one wherein extended release of drug begins after expiration of an initial delay period. A "delayed-rapid" release profile is one wherein rapid release of drug begins after expiration of an initial delay period.

A pulsatile release dosage form is one that provides pulses of high active ingredient concentration, interspersed with low concentration troughs. A pulsatile profile containing two peaks may be described as "bimodal" or "biphasic".

A pseudo-first order release profile is one that approximates a first order release profile. A first order release profile characterizes the release profile of a dosage form that releases a constant percentage of an initial drug charge per unit time.

A pseudo-zero order release profile is one that approximates a zero-order release profile. A zero-order release profile characterizes the release profile of a dosage form that releases a constant amount of drug per unit time.

Subjects. Study population. The subject group of 25 people was defined as generally healthy, though diagnosed disease or condition was not an automatic disqualifier. Individuals with diagnosed pathologies were allowed entry at the discretion of the investigators. Overweight individuals were not excluded unless they meet at least one exclusion criterion below. No randomization occurred as all participants were provided actual supplements; no placebo group was assigned in the study. Participants were recruited from the Healthy Lifestyles patient database.

Inclusion Criteria: Age 18-85 Years

Exclusion Criteria

---

Type 1 diabetes
Severe hypertension, defined as at least 100/180 mmHg.
Any other health condition that may interfere with the study results, as judged by the investigator.
Allergy against any of the ingredients in the tested product.
Any medical condition, in which fiber consumption is contraindicated.
The use of nutritional supplements during the last two months containing one or more similar ingredients, as the tested supplement.
History of alcohol or drug abuse, psychological or other mental issues that are likely to invalidate informed consent, or limit the ability of the patient to comply with the protocol requirements.
Participation in any other studies involving investigational or marketed product concomitantly or within one month prior to entry into the study.
Pregnant or breast feeding.
Persons who eat only 1 meal per day.

---

Criteria for subject discontinuation during the study: (a) Change in the use of a lipid lowering medication, such as starting a statin drug during the study or altering the dose; (b) Patient non-compliance, as defined by taking less than 80% of the supplements as outlined; (c) Being hospitalized; (d) Unable to comply with a proper dosing schedule. Every effort was made to obtain final visit data in participants who discontinue from the study.

Recruitment/centers. Recruitment was performed by Healthy Lifestyles staff and study Investigators.

User instructions. The compositions were intended to control a user's weight, cholesterol, and risk for heart disease and associated metabolic syndrome disorders in a completely natural and safe way.

During the study, a novel combination of compounds was made available to the users that included natural dietary supplement with no expected side effects. The unique combination of fiber complexes and secondary metabolites of the various products was measured to: (1) decrease your appetite while keeping you fuller longer; (2) decrease blood lipid levels; (3) optimize cholesterol ratios; (4) control blood glucose levels; and/or (5) realign the user's microbiome for gut health and improved immune response.

The duration of the project was a period of 3 months during which time one or more of the following was conducted: (1) Blood draw on day 1 for your initial Triglyceride, LDL, HDL, and HbA1C measurements and we will do so again at the conclusion of the study. (2) The user was provided with a µBiome™ microbiome measurement kits along with instructions for use. (3) The individual user was provided with a complete product supply, along with directions for optimal utilization.

TABLE 1

Blood Glucose Data after Taking Bios 7 2x/day for 12 weeks

| Parameter | Percent Reduction |
|---|---|
| Fasting Blood Glucose | −11% |
| HbA1c | −9% |

TABLE 2

Blood Lipid Data after Taking Bios 7 2x/day for 12 weeks

| Total Cholesterol | −10% |
|---|---|
| LDL Cholesterol | −9% |
| VLDL Cholesterol | −6% |
| Cholesterol:HDL Ratio | −4% |
| Triglycerides | −2% |

TABLE 3

Microbiome Data after Taking Bios 7 2x/day for 12 weeks

| Good Bacteria Species | Fold Increase | Bacteria Inversely associated with |
|---|---|---|
| *Lactobacillus* | 38x | Irritable Bowel Syndrome, Diarrhea, Obesity, Type II Diabetes |
| *Roseburia* | 37x | Inflammatory Bowel Disease, Crohn's Disease, Ulcerative Colitis, Type II Diabetes |
| *Prevotella* | 37x | Ulcerative Colitis |
| *Ruminococcus albus* | 28x | Ulcerative Colitis |
| *Akkermansia muciniphila* | 21x | Crohn's Disease, Ulcerative Colitis, Obesity, Type II Diabetes |
| *Bifidobacterium* | 12x | Irritable Bowel Syndrome, Crohn's Disease, Constipation |
| *Oxalobacter formingenes* | 1.8x | Kidney Stones |
| *Odoribacter* | 1.5x | Crohn's Disease, Ulcerative Colitis |
| *Anaerotruncus colihominis* | 1.2x | Obesity |

58% increase in microbial diversity after taking Bios 7 for 12 weeks

TABLE 4

Comparative Data

| Parameter | Bios 7 | Bios Life C | Bios Life 2 |
|---|---|---|---|
| Total Cholesterol | −10% | −8.20% | −4.62% |
| LDL-Cholesterol | −9% | −4.80% | −7.90% |

TABLE 4-continued

Comparative Data

| Parameter | Bios 7 | Bios Life C | Bios Life 2 |
|---|---|---|---|
| HDL Cholesterol | −4.00% | 8.30% | 0 |
| TC/HDL Ratio | −4% | −5.30% | −4% |

Thus, it was found that the present invention surprisingly provided a significant, synergistic effect not expected from the prior art. Specifically, the present invention greatly increased the biodiversity of the intestinal flora (microbiome) of the users in a surprising and unexpected amount. In particular, statistically significant increases in the following healthy bacteria were found, *Lactobacillus, Roseburia, Prevotella, Ruminococcus albus, Akkermansia muciniphila, Bifidobacterium, Oxalobacter formingenes, Odoribacter,* and *Anaerotruncus colihominis*. These bacteria are associated with improved health in those individuals having one or more of the following: Irritable Bowel Syndrome, diarrhea, obesity, Type II Diabetes, Crohn's Disease, ulcerative colitis, kidney stones, Inflammatory Bowel Disease, or constipation.

It is contemplated that any embodiment discussed in this specification can be implemented with respect to any method, kit, reagent, or composition of the invention, and vice versa. Furthermore, compositions of the invention can be used to achieve methods of the invention.

It will be understood that particular embodiments described herein are shown by way of illustration and not as limitations of the invention. The principal features of this invention can be employed in various embodiments without departing from the scope of the invention. Those skilled in the art will recognize, or be able to ascertain using no more than routine experimentation, numerous equivalents to the specific procedures described herein. Such equivalents are considered to be within the scope of this invention and are covered by the claims.

All publications and patent applications mentioned in the specification are indicative of the level of skill of those skilled in the art to which this invention pertains. All publications and patent applications are herein incorporated by reference to the same extent as if each individual publication or patent application was specifically and individually indicated to be incorporated by reference.

The use of the word "a" or "an" when used in conjunction with the term "comprising" in the claims and/or the specification may mean "one," but it is also consistent with the meaning of "one or more," "at least one," and "one or more than one." The use of the term "or" in the claims is used to mean "and/or" unless explicitly indicated to refer to alternatives only or the alternatives are mutually exclusive, although the disclosure supports a definition that refers to only alternatives and "and/or." Throughout this application, the term "about" is used to indicate that a value includes the inherent variation of error for the device, the method being employed to determine the value, or the variation that exists among the study subjects.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps. In embodiments of any of the compositions and methods provided herein, "comprising" may be replaced with "consisting essentially of" or "consisting of". As used herein, the phrase "consisting essentially of" requires the specified integer(s) or steps as well as those that do not materially affect the character or function of the claimed invention. As used herein, the term "consisting" is used to indicate the presence of the recited integer (e.g., a feature, an element, a characteristic, a property, a method/process step or a limitation) or group of integers (e.g., feature(s), element(s), characteristic(s), property(ies), method/process steps or limitation(s)) only.

The term "or combinations thereof" as used herein refers to all permutations and combinations of the listed items preceding the term. For example, "A, B, C, or combinations thereof" is intended to include at least one of: A, B, C, AB, AC, BC, or ABC, and if order is important in a particular context, also BA, CA, CB, CBA, BCA, ACB, BAC, or CAB. Continuing with this example, expressly included are combinations that contain repeats of one or more item or term, such as BB, AAA, AB, BBC, AAABCCCC, CBBAAA, CABABB, and so forth. The skilled artisan will understand that typically there is no limit on the number of items or terms in any combination, unless otherwise apparent from the context.

As used herein, words of approximation such as, without limitation, "about", "substantial" or "substantially" refers to a condition that when so modified is understood to not necessarily be absolute or perfect but would be considered close enough to those of ordinary skill in the art to warrant designating the condition as being present. The extent to which the description may vary will depend on how great a change can be instituted and still have one of ordinary skill in the art recognize the modified feature as still having the required characteristics and capabilities of the unmodified feature. In general, but subject to the preceding discussion, a numerical value herein that is modified by a word of approximation such as "about" may vary from the stated value by at least ±1, 2, 3, 4, 5, 6, 7, 10, 12 or 15%.

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. All such similar substitutes and modifications apparent to those skilled in the art are deemed to be within the spirit, scope and concept of the invention as defined by the appended claims.

To aid the Patent Office, and any readers of any patent issued on this application in interpreting the claims appended hereto, applicants wish to note that they do not intend any of the appended claims to invoke paragraph 6 of 35 U.S.C. § 112, U.S.C. § 112 paragraph (f), or equivalent, as it exists on the date of filing hereof unless the words "means for" or "step for" are explicitly used in the particular claim.

For each of the claims, each dependent claim can depend both from the independent claim and from each of the prior dependent claims for each and every claim so long as the prior claim provides a proper antecedent basis for a claim term or element.

What is claimed is:

1. A solid composition for reducing fasting blood glucose, total cholesterol, LDL cholesterol, VLDL cholesterol, cholesterol:HDL ratio, triglycerides, and increasing a healthy microbiome in a human subject consisting essentially of:
   100-1,500 milligrams of a fiber blend that comprises consisting essentially of fructooligosaccharides guar gum, gum Arabic, locust bean gum, citrus pectin, and oat fiber,
   100-1,500 milligrams of a polyphenol blend consisting essentially of yeast polyphenols, apple extract polyphenols, pomegranate extract polyphenols, and red grape extract polyphenol s,
   100-1,500 milligrams of a multivitamin supplement consisting essentially of Vitamin A, Vitamin C, Vitamin E, Thiamin, Riboflavin, Niacin, Vitamin B12, Biotin, Calcium, and Zinc; and
   wherein the 300-4,500 milligrams of fiber blend, the polyphenol blend, and the multivitamin supplement synergistically lower fasting blood glucose, total cholesterol, LDL cholesterol, VLDL cholesterol, cholesterol:HDL ratio, triglycerides, and synergistically increases the healthy microbiome comprising an increase in *Lactobacillus, Roseburia, Prevotella, Ruminococcus albus, Akkermansia muciniphila, Bifidobacterium, Oxalobacter formingenes, Odoribacter*, and *Anaerotruncus colihominis*, and a decrease in fasting blood glucose, total cholesterol, LDL cholesterol, VLDL cholesterol, cholesterol:HDL ratio, and triglycerides.

2. The composition of claim 1, further comprising one or more excipients, flavorants, sweeteners, or organoleptic agents.

3. The composition of claim 1, wherein the composition has a synergistic effect on the fasting blood glucose, total cholesterol, LDL cholesterol, VLDL cholesterol, cholesterol:HDL ratio, triglycerides, or improving the healthy microbiome when compared to:
   a composition consisting essentially of Guar gum, phytosterols (beta-sitosterol, campestrol, stigmasterol), gum Arabic, locust bean gum, pectin, oat fiber, natural orange flavor, calcium carbonate, ascorbic acid, Vitamin A, beta-carotene, beta glucan, sucralose, niacinamide, d-alpha tocophenyl acetate, chrysanthemum morifolium extract, cyanobalamin, policosanol, zinc gluconate, pyridoxine, riboflavin, folic acid, biotin, thiamine, and chromium; or
   a composition consisting essentially of Guar gum, gum Arabic, locust bean gum, pectin, oat fiber, natural orange flavor, calcium carbonate, ascorbic acid, Vitamin A, beta glucan, Stevia, beta-carotene, niacinamide, d-alpha tocophenyl acetate, maltodextrin, zinc gluconate, pyridoxine, riboflavin, biotin, thiamine, cyanobalamin, chromium, selenium, and folic acid.

4. The composition of claim 1, wherein the composition is provided in an amount that increases microbiome diversity to reduce the symptoms of Irritable Bowel Syndrome, diarrhea, obesity, Type II Diabetes, Crohn's Disease, ulcerative colitis, kidney stones, Inflammatory Bowel Disease, or constipation.

5. The composition of claim 1, wherein the composition lowers at fasting blood glucose, total cholesterol, LDL cholesterol, VLDL cholesterol, cholesterol:HDL ratio, or triglycerides.

6. The composition of claim 1, wherein the composition consists of a fiber blend, a polyphenol blend, a multivitamin supplement, and one or more inactive excipients.

7. The composition of claim 1, wherein the fiber blend consists of fructooligosaccharides and one or more polysaccharides selected from, guar gum, gum Arabic, locust bean gum, citrus pectin, and oat fiber.

8. The composition of claim 1, wherein the polyphenol blend consists of yeast polyphenols, apple extract, polyphenols pomegranate extract polyphenols, and red grape extract.

9. The composition of claim 1, wherein the composition consists of the fiber blend, the polyphenol blend, and the multivitamin supplement.

10. A method for reducing symptoms of Irritable Bowel Syndrome, diarrhea, obesity, Type II Diabetes, Crohn's Disease, ulcerative colitis, kidney stones, Inflammatory Bowel Disease, constipation, by increasing a healthy microbiome in a human subject consisting essentially of:
    identifying a subject in need for reduced fasting blood glucose, total cholesterol, LDL cholesterol, VLDL cholesterol, a cholesterol:HDL ratio, triglycerides, or increased healthy microbiome; and
    providing the subject with a solid composition consisting essentially of 300-4,500 milligrams of guar gum, gum Arabic, locust bean gum, citrus pectin, oat fiber, yeast, apple extract, pomegranate extract, red grape extract, Vitamin A, Vitamin C, Vitamin E, Thiamin, Riboflavin, Niacin, Vitamin B6, Folic acid, Vitamin B12, Biotin, Calcium, and Zinc in an amount sufficient to synergistically lower at fasting blood glucose, total cholesterol, LDL cholesterol, VLDL cholesterol, cholesterol:HDL ratio, triglycerides, or increase the healthy microbiome and reduce the symptoms of Irritable Bowel Syndrome, diarrhea, obesity, Type II Diabetes, Crohn's Disease, ulcerative colitis, kidney stones, Inflammatory Bowel Disease, and constipation.

11. The method of claim 10, wherein the increase in the healthy microbiome comprises an increase in *Lactobacillus, Roseburia, Prevotella, Ruminococcus albus, Akkermansia muciniphila, Bifidobacterium, Oxalobacter formingenes, Odoribacter*, and *Anaerotruncus colihominis*.

12. The method of claim 10, wherein the composition further comprises one or more excipients, flavorants, sweeteners, or organoleptic agents.

13. The method of claim 10, further comprising the step of determining a microbiome of the subject prior to use of the composition and after a predetermined period of time measuring the microbiome to detect changes in the microbiome.

14. The method of claim 10, wherein the composition has a synergistic effect on the fasting blood glucose, total cholesterol, LDL cholesterol, VLDL cholesterol, cholesterol:HDL ratio, triglycerides, or improving the healthy microbiome when compared to a composition without at least one of: fructooligosaccharides, yeast, apple extract, pomegranate extract, or red grape extract.

15. A method of changing a gastrointestinal microbiome to reduce fasting blood glucose, total cholesterol, LDL cholesterol, VLDL cholesterol, cholesterol:HDL ratio, triglycerides, and increase the healthy microbiome of a human subject consisting essentially of:
    administering to the subject a pharmaceutical composition consisting essentially of a glycan therapeutic preparation in an amount effective to treat dysbiosis of the gastrointestinal microbiota, consisting essentially of 300-4,500 milligrams of guar gum, gum Arabic, locust bean gum, citrus pectin, oat fiber, yeast, apple extract, pomegranate extract, red grape extract, Vitamin A, Vitamin C, Vitamin E, Thiamin, Riboflavin, Niacin, Vitamin B6, Folic acid, Vitamin B12, Biotin, Calcium, and Zinc in an amount sufficient to synergistically change the microbiome to reduce fasting blood glucose, total cholesterol, LDL cholesterol, VLDL cholesterol, cholesterol:HDL ratio, and triglycerides, and increases the healthy microbiome comprising *Lactobacillus, Roseburia, Prevotella, Ruminococcus albus, Akkermansia muciniphila, Bifidobacterium, Oxalobacter formingenes, Odoribacter*, and *Anaerotruncus colihominis*.

* * * * *